(12) United States Patent  (10) Patent No.: US 9,211,206 B2
Pryor                      (45) Date of Patent:     Dec. 15, 2015

(54) SHORT HANDLE FOR A LONG STENT

(75) Inventor: Jack Pryor, San Diego, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 2444 days.

(21) Appl. No.: 11/279,599

(22) Filed: Apr. 13, 2006

(65) Prior Publication Data

US 2007/0244540 A1    Oct. 18, 2007

(51) Int. Cl.
*A61F 2/06* (2013.01)
*A61F 2/97* (2013.01)
*A61F 2/95* (2013.01)
*A61F 2/966* (2013.01)

(52) U.S. Cl.
CPC ... *A61F 2/97* (2013.01); *A61F 2/95* (2013.01); *A61F 2/966* (2013.01); *A61F 2002/9517* (2013.01)

(58) Field of Classification Search
CPC ... A61F 2002/9517; A61F 2/97; A61F 2/954; A61F 2002/9522; A61F 2/95; A61F 2002/9528; A61F 2002/9534; A61F 2/958; A61F 2/966; A61M 2025/0188; A61M 25/0029; A61M 2025/0034; A61M 25/0052; A61M 25/0169; A61M 25/0172; A61M 2025/0177; A61M 2025/018; A61M 2025/0183; A61M 25/01; A61M 25/0105; A61M 25/0113; A61M 25/0133; A61M 25/0136; A61M 25/0147
USPC ............................................. 623/1.11, 1.12
See application file for complete search history.

(56) References Cited

U.S. PATENT DOCUMENTS

| 4,744,364 | A | * | 5/1988 | Kensey | 606/213 |
| 4,988,356 | A | * | 1/1991 | Crittenden et al. | 606/192 |
| 5,026,377 | A | * | 6/1991 | Burton et al. | 606/108 |
| 5,195,978 | A | * | 3/1993 | Schiffer | 604/161 |
| 5,201,757 | A | * | 4/1993 | Heyn et al. | 606/198 |
| 5,324,269 | A | * | 6/1994 | Miraki | 604/160 |
| 5,389,087 | A | * | 2/1995 | Miraki | 604/247 |
| 5,433,723 | A |   | 7/1995 | Lindenberg et al. |  |
| 5,690,644 | A | * | 11/1997 | Yurek et al. | 623/1.11 |
| 5,707,376 | A | * | 1/1998 | Kavteladze et al. | 623/1.11 |
| 5,733,267 | A | * | 3/1998 | Del Toro | 623/1.11 |
| 5,776,096 | A | * | 7/1998 | Fields | 604/43 |
| 5,833,694 | A | * | 11/1998 | Poncet | 623/1.11 |
| 5,954,764 | A | * | 9/1999 | Parodi | 623/1.11 |
| 5,968,052 | A | * | 10/1999 | Sullivan et al. | 623/1.11 |
| 6,004,328 | A | * | 12/1999 | Solar | 623/1.11 |
| 6,077,295 | A | * | 6/2000 | Limon et al. | 623/1.11 |
| 6,117,140 | A | * | 9/2000 | Munsinger | A61F 2/95 606/108 |
| 6,120,522 | A | * | 9/2000 | Vrba | A61F 2/95 606/190 |
| 6,254,628 | B1 | * | 7/2001 | Wallace et al. | 623/1.12 |
| 6,494,846 | B1 | * | 12/2002 | Margolis | 600/585 |
| 6,527,746 | B1 | * | 3/2003 | Oslund et al. | 604/160 |

(Continued)

FOREIGN PATENT DOCUMENTS

WO    WO2007/013902    1/2007

*Primary Examiner* — David C Eastwood
*Assistant Examiner* — Erin Colello

(57) ABSTRACT

A stent delivery system for delivering a self-expanding stent includes a keel. The keel is used to pass a pushrod and a guidewire into a sheath through the tubular sidewall of the sheath, i.e., not through the lumen opening at the proximal end of the sheath. Accordingly, the entire length of travel of the proximal end of the sheath during deployment of the stent is not required to be inside of the handle, allowing the handle to be short. Since the handle is short, the handle is easy to manipulate.

18 Claims, 7 Drawing Sheets

(56) References Cited

U.S. PATENT DOCUMENTS

| | | | |
|---|---|---|---|
| 6,527,789 B1* | 3/2003 | Lau et al. | 606/194 |
| 6,599,296 B1 | 7/2003 | Gillick et al. | |
| 6,606,515 B1* | 8/2003 | Windheuser et al. | 600/434 |
| 6,800,065 B2* | 10/2004 | Duane et al. | 604/96.01 |
| 6,893,417 B2* | 5/2005 | Gribbons et al. | 604/103.04 |
| 7,402,141 B2* | 7/2008 | Heuser | 600/585 |
| 2003/0191491 A1* | 10/2003 | Duane | A61M 25/09041 606/194 |
| 2004/0059291 A1* | 3/2004 | McDonnell | A61M 25/0169 604/103.04 |
| 2004/0059369 A1* | 3/2004 | Duffy et al. | 606/194 |
| 2004/0193107 A1* | 9/2004 | Pierpont | A61M 25/1011 604/103.03 |
| 2004/0249434 A1* | 12/2004 | Andreas et al. | 623/1.11 |
| 2005/0010276 A1* | 1/2005 | Acosta et al. | 623/1.11 |
| 2005/0033403 A1* | 2/2005 | Ward et al. | 623/1.11 |
| 2005/0113803 A1* | 5/2005 | Duffy | 604/528 |
| 2005/0119719 A1* | 6/2005 | Wallace et al. | 623/1.11 |
| 2005/0131444 A1* | 6/2005 | Ricci | 606/192 |
| 2005/0149159 A1* | 7/2005 | Andreas et al. | 623/1.11 |
| 2005/0209582 A1* | 9/2005 | Quinn et al. | 604/528 |
| 2005/0222603 A1* | 10/2005 | Andreas et al. | 606/194 |
| 2005/0256562 A1* | 11/2005 | Clerc et al. | 623/1.11 |
| 2005/0288551 A1* | 12/2005 | Callister et al. | 600/115 |
| 2006/0030864 A1* | 2/2006 | Kennedy et al. | 606/108 |
| 2006/0074477 A1* | 4/2006 | Berthiaume et al. | 623/1.11 |
| 2006/0235501 A1* | 10/2006 | Igaki | 623/1.11 |
| 2007/0156225 A1* | 7/2007 | George et al. | 623/1.12 |
| 2008/0091137 A1* | 4/2008 | Reavill | 604/27 |

* cited by examiner

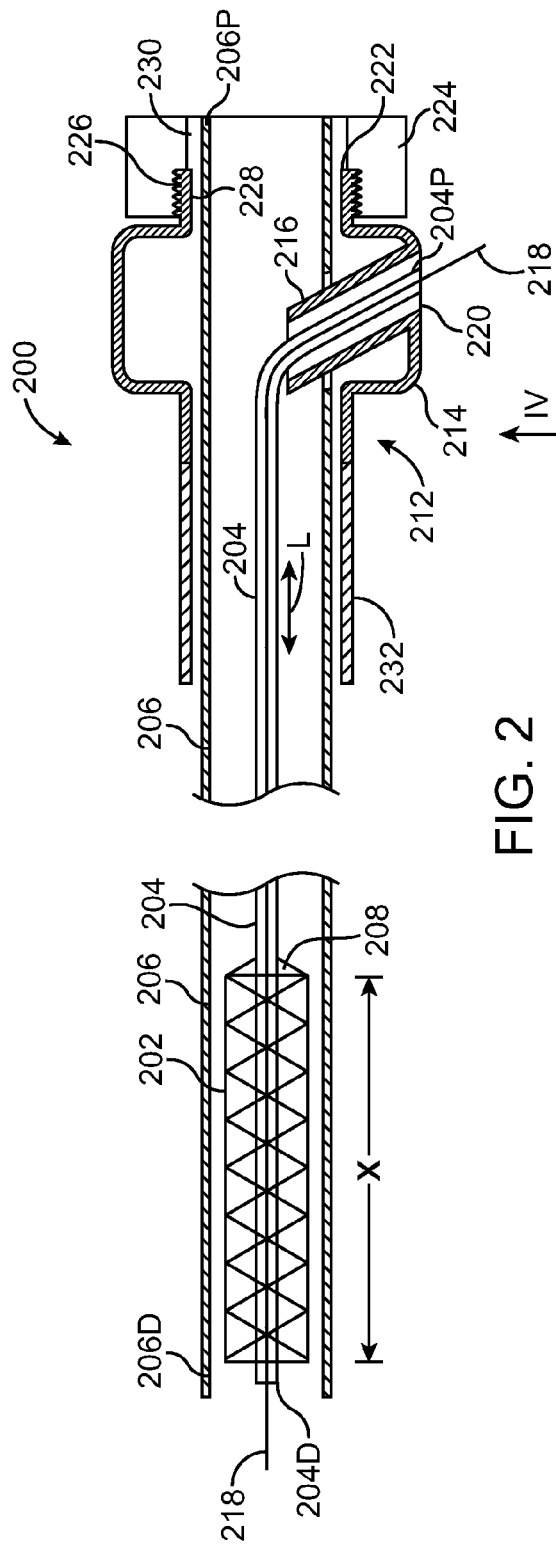
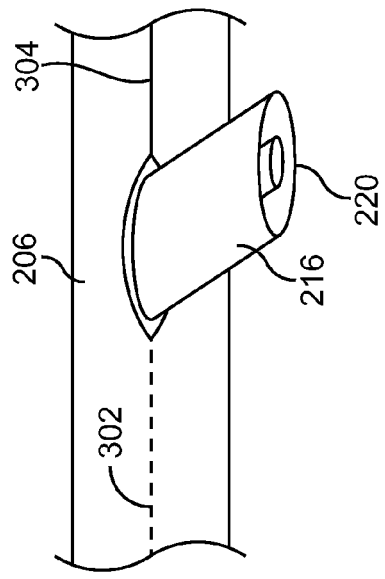

SHORT HANDLE FOR A LONG STENT

BACKGROUND OF THE INVENTION

1. Field of the Invention

The present invention relates to an intra-vascular device and method. More particularly, the present invention relates to a device for deployment of a stent for treatment of luminal, i.e., intra-vascular, diseases.

2. Description of Related Art

In stent deployment systems, a self-expanding stent was restrained within a sheath. After positioning of the stent at the desired location via fluoroscopic guidance, the physician retracted the sheath to deploy the stent, i.e., to expose the stent and allow it to self-expand. To completely deploy the stent, the physician had to retract the sheath over the entire length of the stent, which was relatively cumbersome and typically required the use of both hands of the physician in the case of long self-expanding stents.

To illustrate, FIG. 1 is a partially cutaway delivery system 100 for deploying a stent 102 in accordance with the prior art. Stent 102 is a radially self-expanding stent.

Delivery system 100 includes a pushrod 104 and a sheath 106, sometimes called a catheter sheath. Pushrod 104 includes a distal end 104D and a proximal end 104P. Stent 102 is placed over distal end 104D of pushrod 104 (while in other embodiments of the stent and pushrod, the stent could be located near the distal end of the pushrod which includes being over a portion of an end of the pushrod or being distal to a distal end of the pushrod). Distal end 104D further includes radiopaque markers that allow the location of distal end 104D and stent 102 to be precisely tracked. Proximal end 104P of pushrod 104 terminates within and is mounted to a handle 112 or extends through handle 112 and out a port 114 of handle 112.

Pushrod 104 is a hollow tube which acts as a guide wire lumen. A guide wire 116 can extend through pushrod 104 and distal end 104D. The guide wire 116 can further extend through handle 112 and out port 114.

Sheath 106 includes a distal end 106D and a proximal end 106P. Prior to deployment, stent 102 is radially compressed and restrained within distal end 106D of sheath 106. Proximal end 106P of sheath 106 extends into handle 112. Proximal end 106P of sheath 106 is coupled to an actuation button 118, sometimes called a thumb slider, of handle 112. Sheath 106 is a hollow tube which acts as a pushrod lumen. Pushrod 104 extends through sheath 106.

During use, stent 102 is placed over distal end 104D of pushrod 104 and is radially compressed and restrained within distal end 106D of sheath 106. Stent 102 is introduced intra-vascularly and guided to the treatment site, e.g., an aneurysm.

Once stent 102 is properly positioned, sheath 106 is retracted by retraction of actuation button 118 thus deploying stent 102. More particularly, stent 102 is self-expandable and as sheath 106 is retracted, stent 102 self-expands and is permanently deployed, e.g., anchored within a lumen of a patient. The guiding of a stent and deployment of a self-expanding stent are well known to those of skill in the art.

During deployment, sheath 106 must move the entire linear length X of stent 102 to completely uncover and thus deploy stent 102. Since actuation button 118 is connected to and moves sheath 106, actuation button 118 must also be moved the linear length X to retract sheath 106 over the entire linear length X of stent 102 as actuation button 118 and sheath 106 move in a strictly linear 1:1 motion.

In the case when stent 102 is a long self-expanding stent, length X is substantial, e.g., 200 mm or more. Accordingly, to accommodate the long travel of actuation button 118, handle 112 must also be very long and at least linear length X. However, long handles are cumbersome and difficult to manipulate.

SUMMARY OF THE INVENTION

In accordance with one example, a stent delivery system for delivering a self-expanding stent includes a keel. The keel is used to pass a pushrod and a guidewire into a sheath through the tubular sidewall of the sheath, i.e., not through the lumen opening at the proximal end of the sheath. Accordingly, the entire length of travel of the proximal end of the sheath during deployment of the stent is not required to be inside of the handle, allowing the handle to be short. Since the handle is short, the handle is easy to manipulate.

Embodiments are best understood by reference to the following detailed description when read in conjunction with the accompanying drawings.

BRIEF DESCRIPTION OF THE DRAWINGS

FIG. 2 is a partially cutaway delivery system for deploying a stent in accordance with one embodiment of the present invention;

FIG. 3 is an enlarged bottom perspective view of a sheath and a keel of the delivery system of FIG. 2;

Common reference numerals are used throughout the drawings and detailed description to indicate like elements.

DETAILED DESCRIPTION

Figure 1:
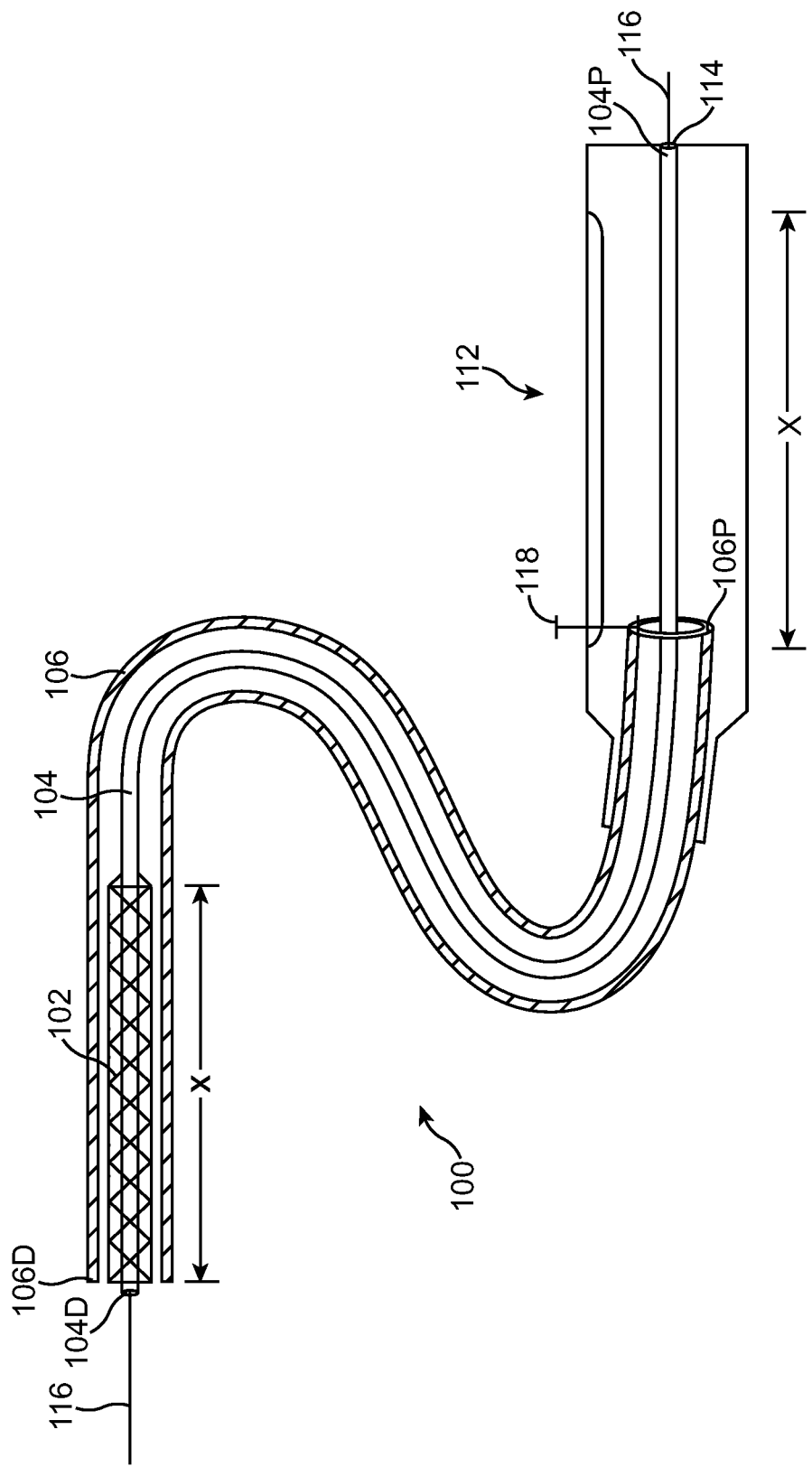
FIG. 1 is a partially cutaway delivery system for deploying a stent in accordance with the prior art.

In accordance with one example, referring to FIGS. 2 and 3 together, a stent delivery system 200 includes a keel 216. Keel 216 is used to pass a pushrod 204 and a guidewire 218 into a sheath 206 through the tubular sidewall of sheath 206, i.e., not through the lumen opening at proximal end 206P of sheath 206. Accordingly, the entire length of travel of proximal end 206P of sheath 206 during deployment of a stent 202 is not required to be inside of handle 212, allowing handle 212 to be short. Since handle 212 is short, handle 212 is easy to manipulate.

More particularly, FIG. 2 is a partially cutaway delivery system 200 for deploying a self-expanding stent 202 in accordance with one embodiment of the present invention. Stent 202 is a radially self-expanding stent having a linear length X, e.g., 200 mm or more.

Delivery system 200 includes a pushrod 204 and a sheath 206, sometimes called a catheter sheath. Pushrod 204, sometimes called an inner member or inner shaft, includes a distal end 204D and a proximal end 204P. As is well known, the proximal end of a delivery system is referenced with respect to the operator's handle while the proximal end of a stent is referenced with respect to the end closest to the heart via the length of blood traveled from the heart.

Stent 202 is placed over distal end 204D of pushrod 204. In one embodiment, distal end 204D further includes radiopaque markers that allow the location of distal end 204D and stent 202 to be precisely tracked. Pushrod 204 includes a stop 208 or other structure to prevent stent 202 from being moved proximally during retraction of sheath 206 as discussed further below.

Proximal end 204P of pushrod 204 terminates within and is mounted to a handle 212. More particularly, handle 212 includes a housing 214. Connected to, or integral with, housing 214 is a keel 216. Proximal end 204P of pushrod 204 is connected to keel 216 and thus to housing 214. Accordingly, pushrod 204 does not move relative to housing 214 of handle 212.

In this example, pushrod 204 is a hollow tube and includes a guide wire lumen. A guide wire 218 extends through pushrod 204 and extends out distal end 204D of pushrod 204. Guide wire 218 further extends out of proximal end 204P of pushrod 204, through keel 216 and out of a guide wire port 220 of keel 216. As illustrated in FIG. 2, pushrod 204 extends through keel 216 such that proximal end 204P of pushrod 204 is located at guide wire port 220 in this example.

Sheath 206 includes a distal end 206D and a proximal end 206P. Prior to deployment, stent 202 is radially compressed and restrained within distal end 206D of sheath 206. Sheath 206 extends through handle 212 and out a sheath port 222 of handle 212. A sheath knob 224 is located on and attached to proximal end 206P of sheath 206.

In one example, sheath knob 224 and housing 214 includes thread 226, 228, respectively, allowing sheath knob 224 to be screwed on to and mounted to housing 214. In accordance with this example, a sheath knob bearing 230 rotatably mounts sheath knob 224 to sheath 206 allowing sheath knob 224 to be unscrewed from housing 214 without rotation of sheath 206.

Coupled to and extending distally from handle 212 is a strain relief 232. Strain relief 232 distributes the bending force over a longer length of the sheath than just a point load at the end of the handle which may create kinking.

FIG. 3 is an enlarged bottom perspective view of sheath 206 and keel 216 of delivery system 200 of FIG. 2. Referring now to FIGS. 2 and 3 together, sheath 206 is a hollow tube formed of a tubular sidewall and includes a pushrod lumen. Keel 216 extends radially inward from the side of housing 214 and penetrates radially into sheath 206 through the tubular sidewall of sheath 206. Accordingly, keel 216 extends from outside of sheath 206, through the tubular sidewall of sheath 206, and into the pushrod lumen of sheath 206.

As discussed further below, during deployment of stent 202, sheath 206 is retracted. As sheath 206 is retracted, sheath 206 moves relative to keel 216. Keel 216, a rigid member, is thus forced against sheath 206 causing keel 216 to split sheath 206.

As illustrated in FIG. 3, in one example, sheath 206 includes a breakaway 302 distal to keel 216 and a slit 304 proximal to keel 316. In accordance with this example, breakaway 302 extends longitudinally along sheath 206, i.e., parallel to longitudinal axis L of sheath 206, distally from keel 316. Generally, breakaway 302 is a region of sheath 206 having less structural integrity than the remainder of sheath 206 such that sheath 206 preferentially splits, sometimes called breaks, at breakaway 302 upon contact with keel 216. Illustratively, breakaway 302 includes one or more perforations, scores, interlocking teeth, a zipper, a slit, or other feature that facilitates splitting of sheath 206 at breakaway 302.

In one example, sheath 206 has elasticity sufficient to allow sheath 206 to be split and pulled around keel 216 without permanent deformation of sheath 206. Accordingly, sheath 206 returns to the cylindrical shape of sheath 206 after being split by keel 216. In accordance with this example, slit 304, e.g., a longitudinal cut in sheath 206, extends longitudinally proximally from keel 216.

As set forth above, sheath 206 is a hollow tube and includes a pushrod lumen. Pushrod 204 extends through keel 216 and into sheath 206.

During use, stent 202 is placed over distal end 204D of pushrod 204 and is radially compressed and restrained within distal end 206D of sheath 206. Stent 202 is introduced intravascularly and guided to the treatment site, e.g., a stenosis or narrowing of the vascular vessel.

Once stent 202 is properly positioned, sheath 206 is retracted by retraction of sheath knob 224. For example, sheath knob 224 is unscrewed from housing 214. Sheath knob 224 is pulled from housing 214, e.g., by the physician, thus retracting sheath 206. Stent 202 is self-expandable and as sheath 206 is retracted, stent 202 self-expands as it is uncovered and is permanently deployed, e.g., anchored within a lumen of a patient.

During deployment, sheath 206 moves (is retracted) at least the entire length X of stent 202 to completely uncover and thus deploy stent 202. Since retraction of sheath 206 is accomplished by pulling of sheath 206 out of handle 212, handle 212 can be much shorter than stent 202.

Figure 4:
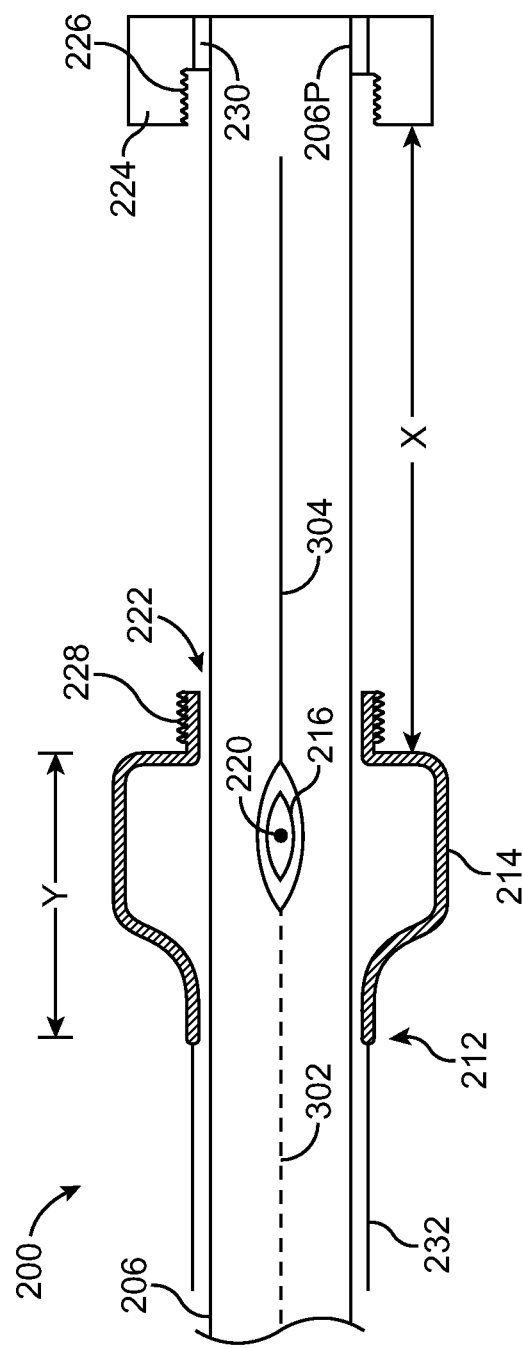
FIG. 4 is a partially cutaway view of the delivery system taken from the bottom along a line IV of FIG. 2 after deployment of the stent.

FIG. 4 is a partially cutaway view of delivery system 200 taken from the bottom along line IV of FIG. 2 after deployment of stent 202. As shown, sheath 206 moves (is retracted) at least the entire length X of stent 202 (see FIG. 2) to completely uncover and thus deploy stent 202. Illustratively, handle 212 has a linear length Y less than linear length X of stent 202.

More particularly, keel 216 is used to pass pushrod 204 and guidewire 218 into sheath 206 through the tubular sidewall of sheath 206, i.e., not through the pushrod lumen opening at proximal end 206P of sheath 206. Accordingly, the entire length of travel of proximal end 206P is not required to be inside of handle 212, allowing handle 212 to be short. Since handle 212 is short, handle 212 is easy to manipulate.

Figure 5:
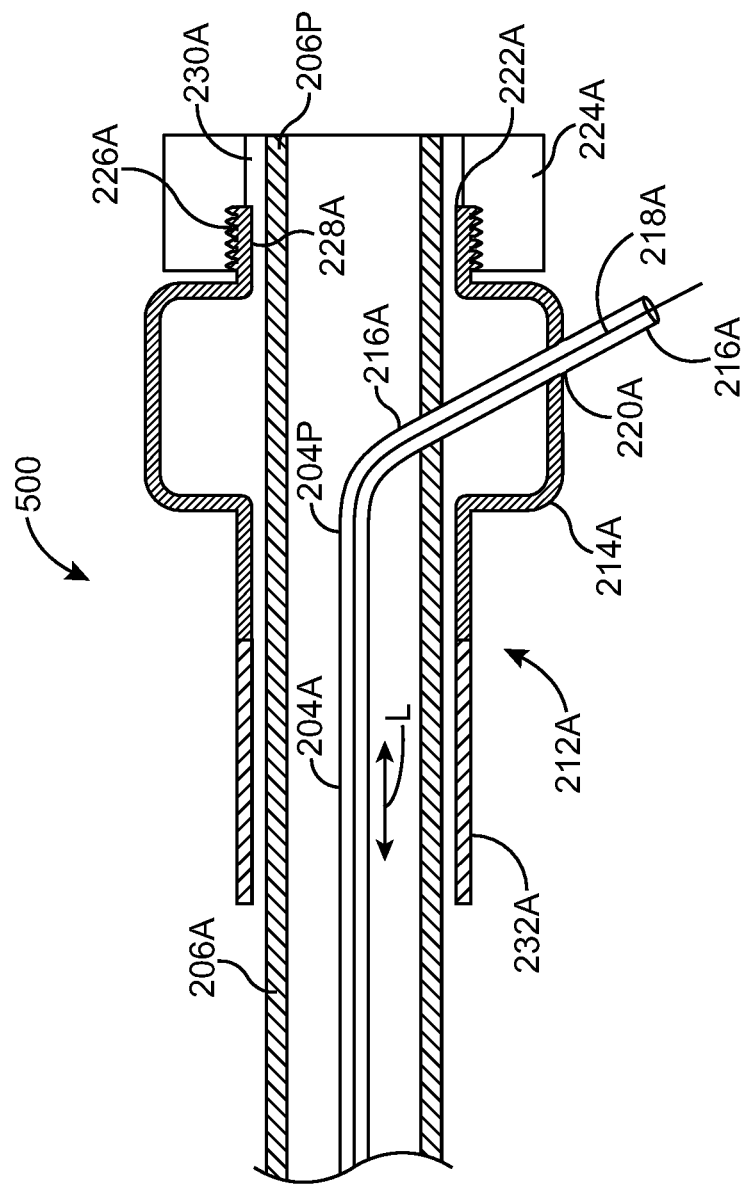
FIG. 5 is a partially cutaway delivery system for deploying a self-expanding stent in accordance with another embodiment of the present invention.

FIG. 5 is a partially cutaway delivery system 500 for deploying a self-expanding stent in accordance with another embodiment of the present invention. Pushrod 204A, sheath 206A, handle 212A, housing 214A, guide wire 218A, guide wire port 220A, sheath port 222A, sheath knob 224A, threads 226A, 228A, bearing 230A, and strain relief 232A of delivery system 500 of FIG. 5 are similar to pushrod 204, sheath 206, handle 212, housing 214, guide wire 218, guide wire port 220, sheath port 222, sheath knob 224, threads 226, 228, bearing 230, and strain relief 232 of delivery system 200 of FIG. 2, respectively, and so are not discussed further.

Referring now to FIG. 5, in accordance with this example, keel 216A is directly attached to (or integral with) proximal end 204P of pushrod 204A, for example, with adhesive, welding, threads, or mechanical fasteners. Stated another way, keel 216A is an extension of pushrod 204A that passes from within sheath 206A, through the cylindrical, sometimes called tubular, sidewall of sheath 206A, and to housing 214A of handle 212A. In one example, as indicated by the dashed line, keel 216A protrudes outside from housing 214A.

Guide wire 218A passes through guide wire port 220A and into keel 216A, passes through keel 216A and into sheath 206A, and from keel 216A passes into pushrod 204A. Use of keel 216A allows handle 212A to be short and easy to manipulate.

Figure 6:
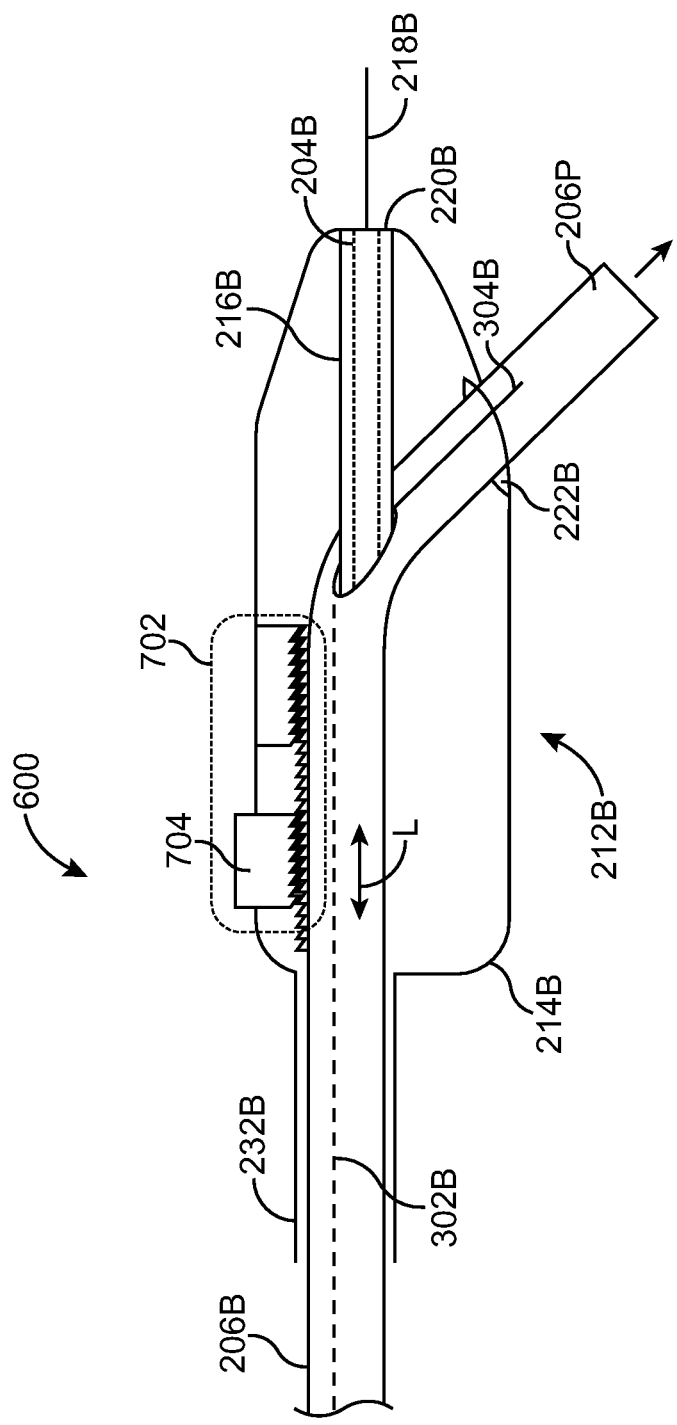
FIG. 6 is a partially cutaway delivery system for deploying a self-expanding stent in accordance with yet another embodiment of the present invention.

FIG. 6 is a partially cutaway delivery system 600 for deploying a self-expanding stent in accordance with yet another embodiment of the present invention. Pushrod 204B, sheath 206B, handle 212B, housing 214B, guide wire 218B, guide wire port 220B, sheath port 222B, strain relief 232B, breakaway 302B, and slit 304B of delivery system 600 of FIG. 6 are similar to pushrod 204, sheath 206, handle 212, housing 214, guide wire 218, guide wire port 220, sheath port 222, strain relief 232, breakaway 302, and slit 304 of delivery system 200 of FIGS. 2 and 3, respectively, and so are not discussed further.

Referring now to FIG. 6, in accordance with this example, keel 216B extends distally from the rear of housing 214B and penetrates into sheath 206B. In accordance with this configuration, pushrod 204B extends straight through handle 212B and without any significant bending. Recall in delivery system 200 of FIG. 2, sheath 206 extends straight through handle 212 and pushrod 204 bends radially outward to extend through both keel 216 and the tubular sidewall of sheath 206 to the side of housing 214.

However, referring still to FIG. 6, sheath 206B is bent radially outwardly to extend out the side of housing 214B through sheath port 222B. Further, in accordance with this example, sheath 206B is retracted by use of a ratchet mechanism 702.

Figure 7:
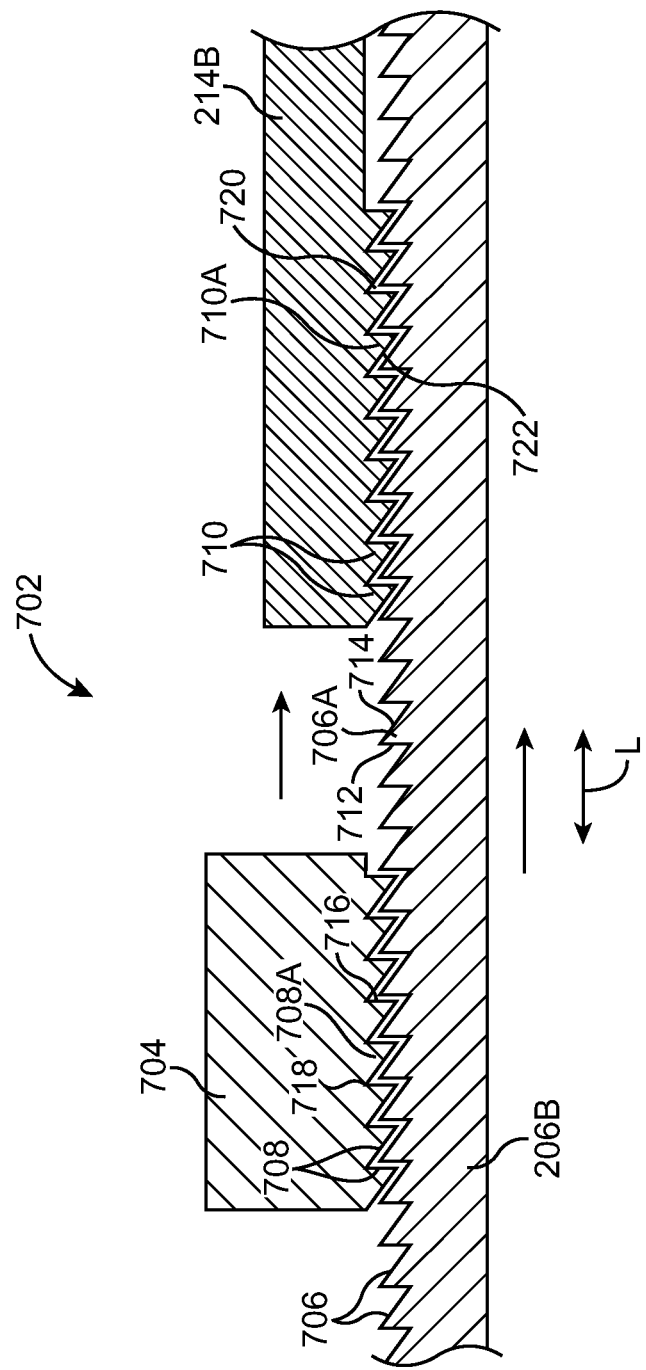
FIG. 7 is a cross-sectional view of a ratchet mechanism of the delivery system of FIG. 6.

FIG. 7 is a cross-sectional view of ratchet mechanism 702 of delivery system 600 of FIG. 6. Referring now to FIGS. 6 and 7 together, ratchet mechanism 702 includes a thumb slider 704 slidably attached to housing 214B.

Specifically, the physician retracts, i.e., moves proximally, thumb slider 704 to retract sheath 206B. Once thumb slider 704 is fully retracted, i.e., moved proximally to the end of travel of thumb slider 704 such that thumb slider 704 is in abutting contact with housing 214B, thumb slider 704 is advanced, i.e., moved distally. However, sheath 206B is engaged with housing 214B such that thumb slider 704 is advanced without advancement of sheath 206B. This procedure is continuously repeated to retract sheath 206B to deploy the stent. As sheath 206B is retracted, sheath 206B feeds out of sheath port 222B.

Referring now to FIG. 7, in accordance with this example, sheath 206B includes teeth 706. Similarly, thumb slider 704 includes teeth 708 and housing 214B includes teeth 710. Teeth 706 of sheath 206B slide only proximally relative to teeth 708, 710 of thumb slider 704 and housing 214B, respectively. Conversely, teeth 706 of sheath 206B do not slide distally relative to teeth 708, 710 of thumb slider 704 and housing 214B, respectively. This facilitates one-way proximal motion of sheath 206B, i.e., retraction of sheath 206, relative to thumb slider 704 and housing 214B as set forth in greater detail below.

To illustrate, a first tooth 706A of teeth 706 of sheath 206B includes an engagement surface 712 and a sliding surface 714. Engagement surface 712 is distal to sliding surface 714. Further, engagement surface 712 is radially perpendicular to longitudinal axis L of sheath 206B. Conversely, sliding surface 714 extends from engagement surface 712 proximally inward and at an angle to engagement surface 712.

To further illustrate, a first tooth 708A of teeth 708 of thumb slider 704 includes an engagement surface 716 and a sliding surface 718. Engagement surface 716 is proximal to sliding surface 718. Further, engagement surface 716 is radially perpendicular to longitudinal axis L of sheath 206B. Conversely, sliding surface 718 extends from engagement surface 712 distally outward and at an angle to engagement surface 716.

To further illustrate, a first tooth 710A of teeth 710 of housing 214B includes an engagement surface 720 and a sliding surface 722. Engagement surface 720 is proximal to sliding surface 722. Further, engagement surface 720 is radially perpendicular to longitudinal axis L of sheath 206B. Conversely, sliding surface 722 extends from engagement surface 720 distally outward and at an angle to engagement surface 720.

Retraction of thumb slider 704 causes engagement surfaces 716 of teeth 708 of thumb slider 704 to engage engagement surfaces 712 of teeth 706 of sheath 206B. Accordingly, retraction of thumb slider 704 causes retraction of sheath 206B. As sheath 206B is retracted, slider surfaces 714 of teeth 706 of sheath 206B slide against slider surfaces 722 of teeth 710 of housing 214B. Stated another way, as sheath 206B is retracted, teeth 706 of sheath 206B slide past teeth 710 of housing 214B.

Once thumb slider 704 reaches the end of its proximal travel, thumb slider 704 is advanced, i.e., moved distally. However, engagement surfaces 712 of teeth 706 of sheath 206B engage engagement surfaces 720 of teeth 710 of housing 214B preventing advancement of sheath 206B relative to housing 214B. Further, as thumb slider 704 is advanced, slider surfaces 718 of teeth 708 of thumb slider 704 slide against slider surfaces 714 of teeth 706 of sheath 206B. Stated another way, as thumb slider 704 is advanced, teeth 708 of thumb slider 704 slide past teeth 706 of sheath 206B. Referring again to FIG. 6, use of keel 216B and ratchet mechanism 702 allows handle 212B to be short and easy to manipulate.

Figure 8:
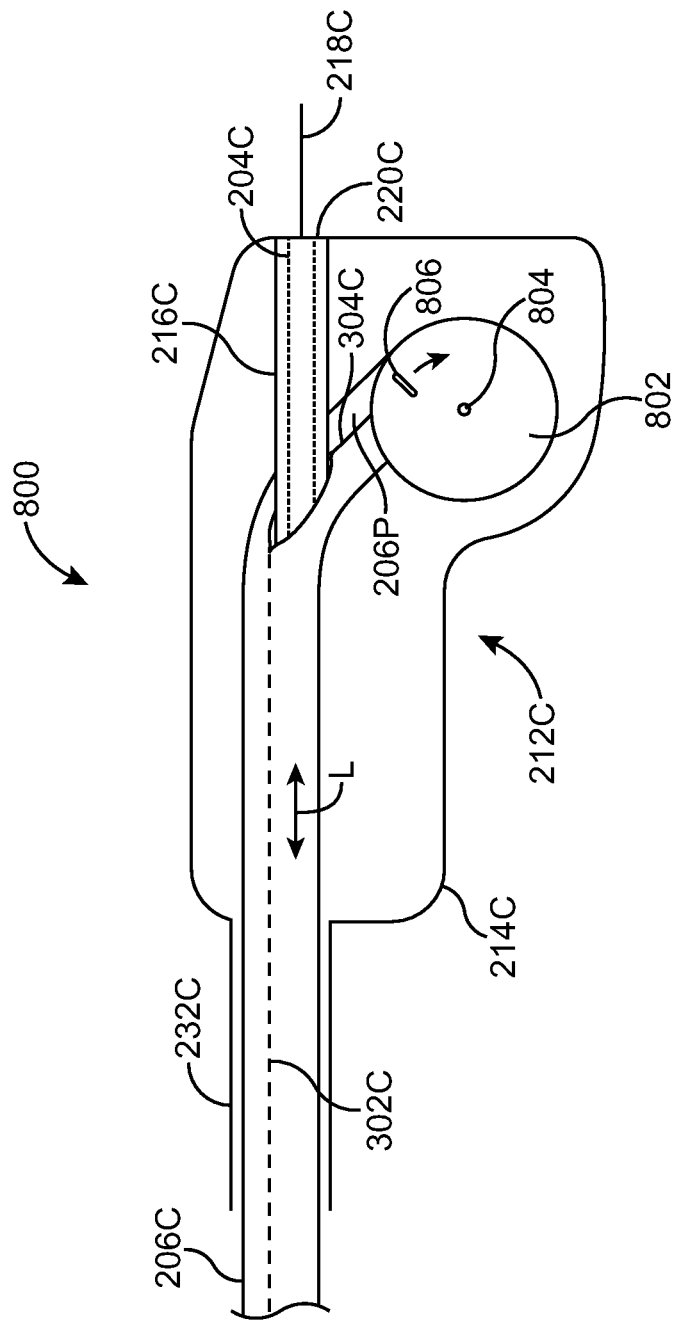
FIG. 8 is a partially cutaway delivery system for deploying a self-expanding stent in accordance with another embodiment of the present invention.

FIG. 8 is a partially cutaway delivery system 800 for deploying a self-expanding stent in accordance with another embodiment of the present invention. Pushrod 204C, sheath 206C, handle 212C, housing 214C, guide wire 218C, guide wire port 220C, strain relief 232C, breakaway 302C, and slit 304C of delivery system 800 of FIG. 8 are similar to pushrod 204B, sheath 206B (absent teeth 706), handle 212B, housing 214B, guide wire 218B, guide wire port 220B, strain relief 232B, breakaway 302B, and slit 304B of delivery system 600 of FIG. 6, respectively, and so are not discussed further.

Referring now to FIG. 8, in accordance with this example, handle 212C includes a spool 802 coupled to housing 214C. More particularly, spool 802 rotates on an axle 804 extending through spool 802 and coupled to housing 214C.

Proximal end 206P of sheath 206C is connected to spool 802. Spool 802, sometimes called a coil, provides a means for retracting sheath 206C. In this example, spool 802 includes a spool knob 806 that is rotated by the physician thus rotating spool 802 around axle 804. As spool 802 rotates, sheath 206C is wound into spool 802 and thus retracted.

By winding (coiling) sheath 206C around spool 802, handle 212C can be much shorter than the length of the stent. Since handle 212C is short, handle 212C is easy to manipulate.

This disclosure provides exemplary embodiments of the present invention. The scope of the present invention is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A stent delivery system comprising:
   a handle comprising a housing and a keel directly coupled to said housing;
   a pushrod having a proximal end connected to said keel of said handle such that said keel and said pushrod do not move relative to said housing;
   a stent located over a distal end of said pushrod; and
   a sheath constraining said stent at a distal end of said sheath, said keel extending from said housing and into said sheath through a sidewall of said sheath; and a sheath knob attached to a proximal end of said sheath; wherein said sheath knob is threadedly mounted to said housing.

2. The stent delivery system of claim 1 wherein said handle has a linear length less than a linear length of said stent.

3. The stent delivery system of claim 1 wherein said pushrod comprises a guide wire lumen, said stent delivery system further comprising a guide wire extending through said pushrod.

4. The stent delivery system of claim 3 wherein said keel comprises a guide wire port, said guide wire extending out a proximal end of said pushrod, through said keel, and out said guide wire port.

5. The stent delivery system of claim 1 wherein said sheath comprises a pushrod lumen, said keel extending from outside of said sheath, through said tubular sidewall of said sheath, and into said pushrod lumen.

6. The stent delivery system of claim 1 further comprising a strain relief coupled to said handle.

7. The stent delivery system of claim 6 wherein said strain relief relieves strain between said pushrod, said sheath, and said handle.

8. The stent delivery system of claim 1 further comprising a sheath knob bearing rotatably mounting said sheath knob to said sheath.

9. The stent delivery system of claim 1 wherein said sheath comprises a breakaway distal to said keel.

10. The stent delivery system of claim 9 wherein said breakaway extends longitudinally along said sheath.

11. The stent delivery system of claim 9 wherein said breakaway breaks upon contact with said keel.

12. The stent delivery system of claim 11 wherein said breakaway is a region of said sheath having less structural integrity than a remainder of said sheath.

13. The stent delivery system of claim 9 wherein said breakaway is selected from the group consisting of one or more perforations, scores, interlocking teeth, a zipper, and a slit.

14. The stent delivery system of claim 1 wherein said sheath comprises a slit proximal to said keel.

15. The stent delivery system of claim 14 wherein said slit extends longitudinally along said sheath.

16. The stent delivery system of claim 14 wherein said slit comprises a longitudinal cut in said sheath.

17. The stent delivery system of claim 1 wherein said proximal end of said pushrod is directly attached to said keel.

18. The stent delivery system of claim 17 wherein said keel protrudes outside from said housing.

* * * * *